(12) United States Patent
Campin et al.

(10) Patent No.: US 6,554,429 B1
(45) Date of Patent: Apr. 29, 2003

(54) METHOD FOR DETERMINING ACCOMMODATION

(75) Inventors: John A. Campin, Orlando, FL (US);
Gary P. Gray, Orlando, FL (US);
George Pettit, Maitland, FL (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 09/977,538

(22) Filed: Oct. 15, 2001

(51) Int. Cl.⁷ .................................................. A61B 3/10
(52) U.S. Cl. ........................................ 351/211; 351/246
(58) Field of Search ................................. 351/211, 212, 351/216, 222, 237, 239, 241, 243, 246

(56) References Cited

U.S. PATENT DOCUMENTS

| 5,442,412 A | 8/1995 | Frey et al. |
| 5,632,742 A | 5/1997 | Frey et al. |
| 5,777,719 A | 7/1998 | Williams et al. |
| 5,949,521 A | 9/1999 | Williams et al. |
| 5,963,300 A | * 10/1999 | Horwitz ...................... 351/209 |
| 6,095,651 A | 8/2000 | Williams et al. |
| 6,270,221 B1 | 8/2001 | Liang et al. |
| 6,271,914 B1 | 8/2001 | Liang et al. |

FOREIGN PATENT DOCUMENTS

| EP | 1 153 570 A1 | 11/2001 |
| WO | WO 00/10448 | 3/2000 |
| WO | WO 01/87201 A1 | 11/2001 |

* cited by examiner

Primary Examiner—George Manuel
(74) Attorney, Agent, or Firm—Jeffrey S. Schira

(57) ABSTRACT

An automated, objective method for determining the accommodative range and aberration profile of an eye using a wavefront sensor that iteratively determines the change in accommodation of the lens of an eye.

2 Claims, 2 Drawing Sheets

METHOD FOR DETERMINING ACCOMMODATION

BACKGROUND OF THE INVENTION

This invention relates generally to the field of ophthalmic diagnostic devices and, more particularly, to wavefront sensors used as diagnostic devices.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In the normal, healthy eye, sharp images are formed on the retina (emmetropia). In many eyes, images are either formed in front of the retina because the eye is abnormally long (axial myopia), or formed in back of the retina because the eye is abnormally short (axial hyperopia). The cornea also may be asymmetric or toric, resulting in an uncompensated cylindrical refractive error referred to as corneal astigmatism. In addition, due to age-related reduction in lens accommodation, the eye may become presbyopic resulting in the need for a bifocal or multifocal correction device.

In the past, axial myopia, axial hyperopia and corneal astigmatism generally have been corrected by spectacles or contact lenses, but there are several refractive surgical procedures that have been investigated and used since 1949. Barraquer investigated a procedure called keratomileusis that reshaped the cornea using a microkeratome and a cryolathe. This procedure was never widely accepted by surgeons. Another procedure that has gained widespread acceptance is radial and/or transverse incisional keratotomy (RK or AK, respectively). In the 1990s, the use of photoablative lasers to reshape the surface of the cornea (photorefractive keratectomy or PRK) or for mid-stromal photoablation (Laser-Assisted In Situ Keratomileusis or LASIK) have been approved by regulatory authorities in the U.S. and other countries.

In the past, the amount of tissue removed by the laser was determined by taking pre-operative measurements of the optical errors of the eye, sphere, cylinder and axis, termed "low order" optical aberrations. These measurements were manually loaded into the refractive laser and a proposed corrective "recipe" was calculated by the laser software. More recently, the use of wavefront sensor technology, which measures both the low order optical aberrations and the "higher" order aberrations, such as coma, trefoil and spherical aberrations, have been investigated. See for example U.S. Pat. Nos. 5,777,719, 5,949,521, 6,095,651 (Williams, et al.), U.S. patent application Ser. Nos. 09/566,409 and 09/566,668, both filed May 8, 2000, and in PCT Patent Publication No. WO 00/10448, the entire contents of which being incorporated herein by reference. These wavefront sensors are particularly useful when used in combination with a high-speed eye movement tracker, such as the tracker disclosed in U.S. Pat. Nos. 5,442,412 and 5,632,742 (Frey, et al.), the entire contents of which being incorporated herein by reference. The ultimate goal of these devices is to link the wavefront sensor to the laser and eye movement tracker to provide real-time diagnostic data to the laser during surgery. In the past, as best seen in FIG. 1, in order to focus wavefront sensing device 10, the patient was seated at the device so that the patient's eye 12 views fixation target 14 though optical pathway 16 that includes adjustable focus mechanism 18. Mechanism 18 compensates for defocus error (and possibly astigmatism) to allow the patient to see fixation target 14 relatively clearly regardless of the refractive error in the patient's eye 12. Video camera 20, disposed along optical pathway 22 allows device 10 operator (not shown) to position eye 12 relative to device 10. Once the patient is in the correct position and is viewing fixation target 14, probe beam 24 of optical radiation is sent into eye 12. A fraction of the radiation is scattered by the retina exits the eye in the form of a re-emitted wavefront. Optical pathway 26 conveys this wavefront to the entrance face of wavefront sensor 28.

The lens of the eye is a dynamic element, capable of changing the effective focal length of the eye through accommodation. In performing wavefront measurements, it is important to take this accommodative ability into account. Normally, the wavefront is measured with the lens as relaxed as possible, so that the eye is minimally refracting (most hyperopic). Relaxing the lens is typically achieved by adjusting the focus mechanism in the fixation pathway so that the fixation target appears to lie just beyond the patient's most hyperopic focal point. The fixation target in this instance will appear slightly out of focus to the patient. This process is known as "fogging".

Prior to the present invention, wavefront sensors were typically only used to measure the refractive error of an eye when the eye was in its most relaxed or hyperopic state. The inventors have discovered that a wavefront sensor can be used to measure the range of accommodation of an eye, and to measure optical aberrations over the accommodative range. This capability may have diagnostic utility in characterizing age-related changes in performance of the crystalline lens and in interpreting certain visual symptoms. This capability may also allow for customization of the ablation pattern of the refractive laser to optimize the patient's vision at any accommodative state (i.e., at any desired focal point in front of the eye).

Accordingly, a need continues to exist for a method of determining the accommodative range of an eye.

BRIEF SUMMARY OF THE INVENTION

The present invention improves upon the prior art by providing an automated objective method for determining the accommodative range and aberration profile of an eye using a wavefront sensor that iteratively determines the change in accommodation of the lens of an eye.

Accordingly, one objective of the present invention is to provide an automated objective accommodative measurement method.

Another objective of the present invention is to provide an automated aberration profile measurement method.

Another objective of the present invention is to provide an accommodation measurement method for a wavefront sensor that does not require subjective determination of accommodation.

Another objective of the present invention is to provide an accommodation measurement method for a wavefront sensor that does not require participation by a skilled operator.

These and other advantages and objectives of the present invention will become apparent from the detailed description and claims that follow.

DETAILED DESCRIPTION OF THE INVENTION

The method of the present invention may be practiced on any commercially available wavefront sensor having appropriate software controls. Suitable devices are disclosed in U.S. Pat. Nos. 5,777,719, 5,949,521, 6,095,651, U.S. patent application Ser. Nos. 09/566,409 and 09/566,668, both filed May 8, 2000, and in PCT Publication No. WO 00/10448. The method of the present invention requires that the eye initially be fogged, which can include an iterative process wherein the wavefront sensor first calculates a stable effective clinical prescription for the eye being measured. The prescription is then moved in the hyperopic direction until the emanating wavefront is stable at the eye's most hyperopic state. These steps "fog" the eye in preparation for the method of the present invention.

Figure 2:
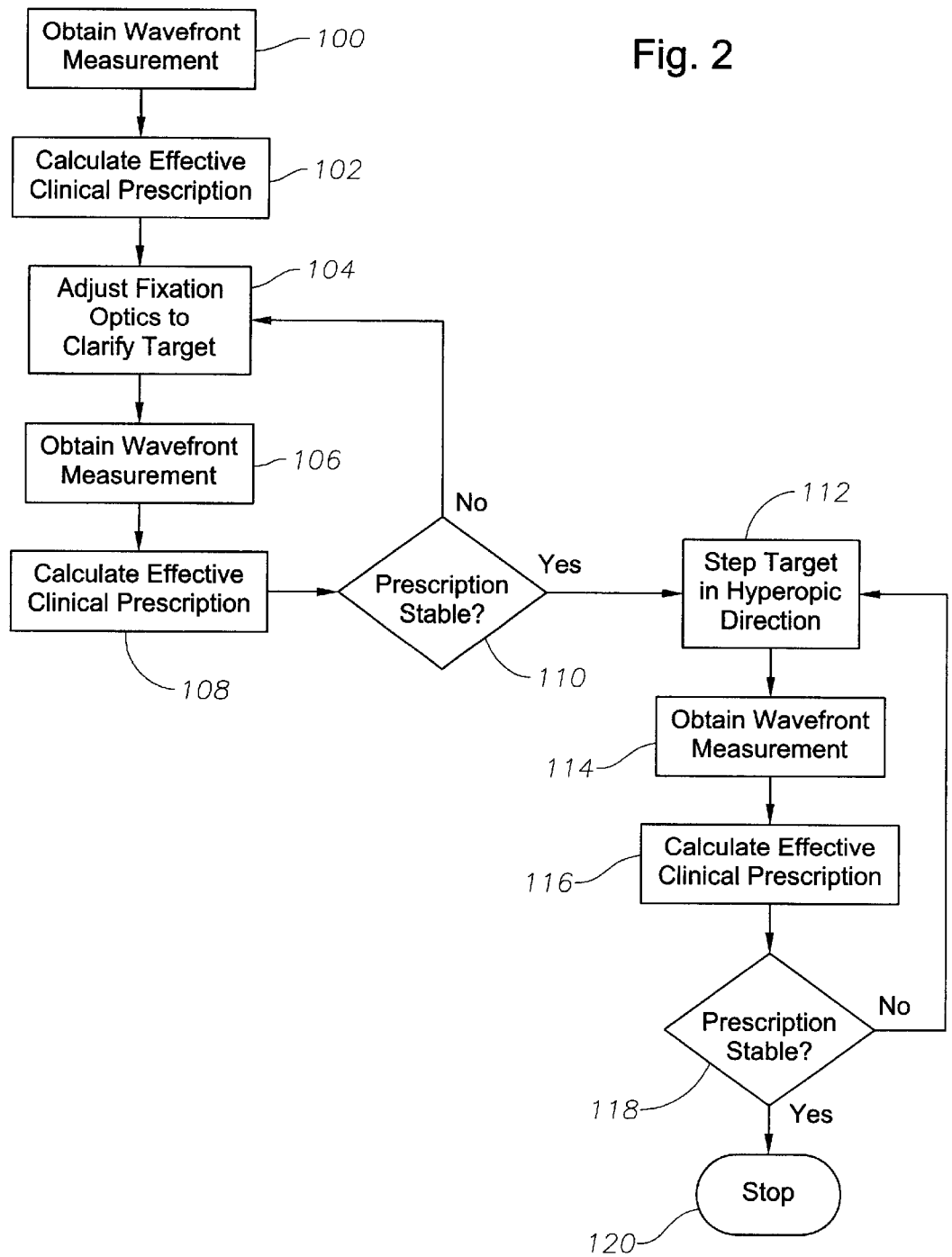
FIG. 2 is a flow chart illustrating a fogging method that may be used with the present invention.

As best seen in FIG. 2, one preferred method of fogging the eye involves initially having the patient view fixation target 14 with focus mechanism 18 in its nominal position, which is the appropriate position for an eye with no significant defocus or astigmatic error. As patient eye 12 attempts to view this target, initial wavefront measurement is taken at step 100. The effective clinical prescription for eye 12 is calculated at step 102 from the measurement taken at step 100 and focus mechanism 18 is adjusted at step 104 based on the prescription calculated at step 102 to correct for any detected defocus or astigmatic error. A second wavefront measurement is taken at step 106 and the effective clinical prescription for eye 12 is calculated at step 108 from the measurement taken at step 106. The difference between the prescription calculated at step 102 and the prescription calculated at step 106 is determined during step 110. If the two prescriptions are not within allowed tolerances, such as approximately 0.25 diopters (other tolerances may also be used), steps 104 through 110 are repeated iteratively until a stable prescription is obtained (e.g., the difference between the two prescriptions is within the allowed tolerance for defocus and astigmatic errors, including the axis of any detected astigmatism).

Once a stable prescription is obtained at step 110, focusing mechanism 18 is adjusted in discrete, defined steps (for example, 0.5 diopters or other suitable amount) in the hyperopic direction during step 112, and an initial wavefront measurement is taken at step 114. This, in effect, applies an accommodative stimulus to eye 12. The effective clinical prescription for eye 12 is calculated at step 116 from the measurement taken at step 114. The prescription calculated at step 116 is analyzed at step 118 to see if the prescription has also moved in the hyperopic direction by more than a threshold amount, such as approximately 0.25 diopters. If the prescription has not moved in the hyperopic direction by more than a threshold amount, then the prescription is deemed stable and eye 12 suitably fogged for accurate wavefront measurements. If the prescription has moved in the hyperopic direction by more than the threshold amount, the prescription is deemed not to be stable, and steps 112 through 118 are repeated iteratively until a stable prescription is obtained.

Figure 1:
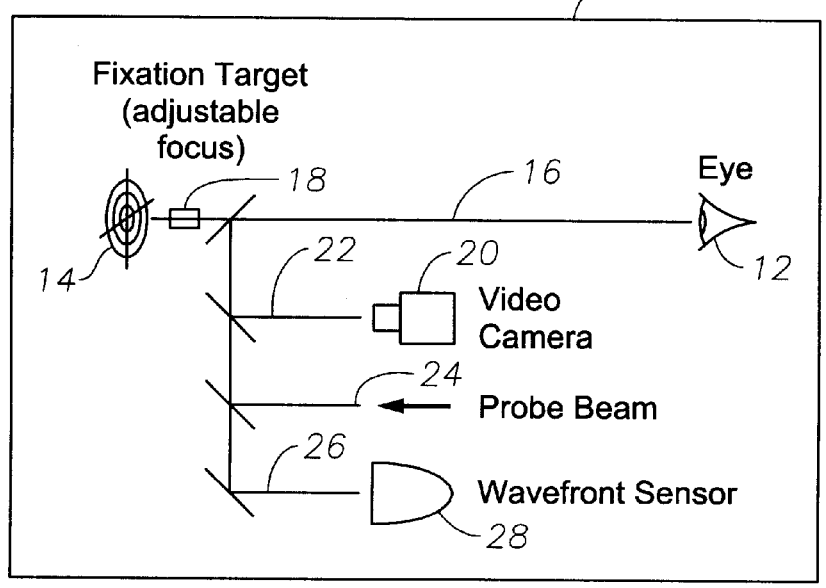
FIG. 1 is a simplified schematic representation of a prior art wavefront sensing device.
Figure 3:
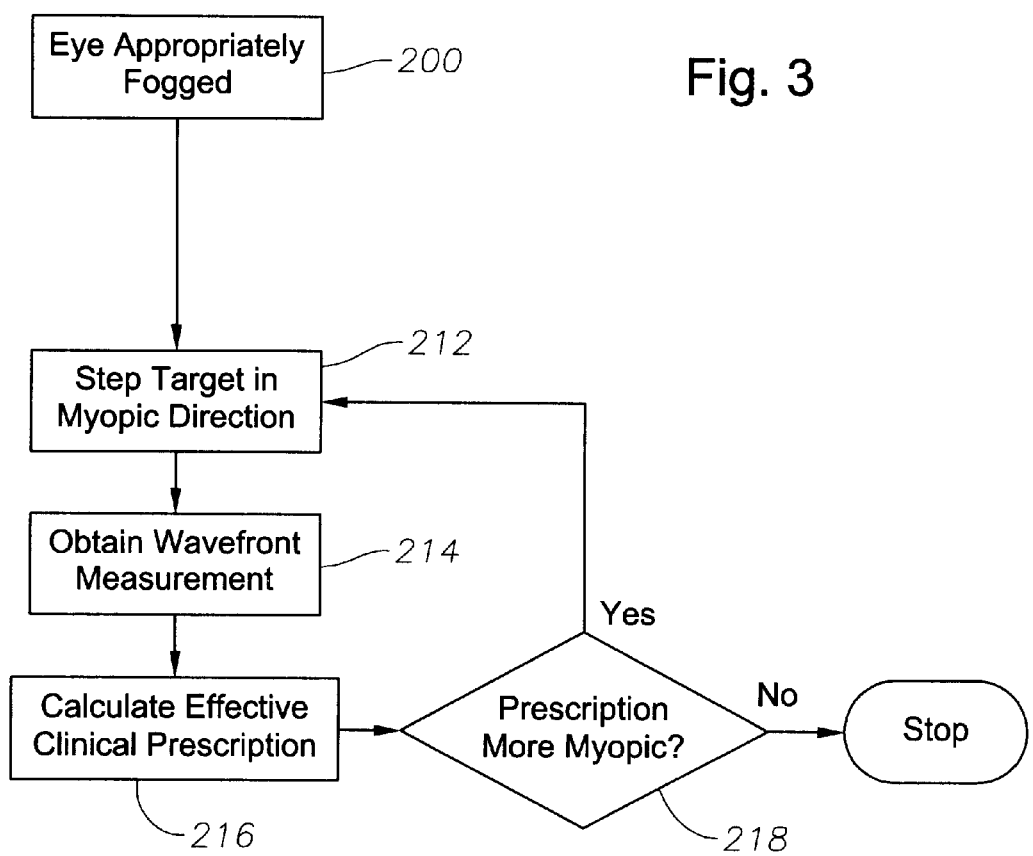
FIG. 3 is a flow chart illustrating the accommodation measurement method of the present invention.

As best seen in FIG. 3, once eye 12 has been appropriately fogged at step 200, focusing mechanism 18 is adjusted in discrete, defined steps in the myopic direction during step 212, and a wavefront measurement is taken at step 214. The effective clinical prescription for eye 12 is calculated at step 216 from the measurement taken at step 214. The prescription calculated at step 216 is analyzed at step 218 to see if the prescription has also moved in the myopic direction by more than a threshold amount, such as approximately 0.25 diopters. If the prescription has not moved in the myopic direction by more than a threshold amount, then the prescription is deemed stable and the accommodative range of eye 12 is known to lie between the stable myopic prescription calculated at step 216, and the stable hyperopic prescription calculated at step 116. If the prescription has moved in the myopic direction by more than the threshold amount, the prescription is deemed not to be stable, and steps 212 through 218 are repeated iteratively until a stable prescription is obtained. In this manner, the entire accommodative range of eye 12 can be determined.

In some cases, patients may have difficulty viewing target 14 and complying with the test. In order to facilitate measurement of such patients, additional logic may be added. For example, a sudden large hyperopic change in the wavefront may indicate that the patient has lost fixation. Adjusting focus mechanism 18 by a substantial amount (e.g., one diopter) in the hyperopic direction may allow the patient to regain fixation and resume the accommodation testing.

In addition to measuring the accommodative range of eye 12, the method of the present invention can also be used to customize the outcome of laser refractive surgery. For example, since the wavefront and corrective prescription for eye 12 is known throughout the entire accommodative range, the laser refractive surgery can be optimized at any particular focal length depending upon the desires of the patient. Therefore, if the patient desires optimum focus at one meter, the prescription that will optimize the refractive correction at a one meter focal length may be used. Similarly, if the patient desires optimum focus at infinity, or at the point of maximal accommodation, the final prescription calculated at step 116 or at 216, respectively, may be used.

This description is given for purposes of illustration and explanation. It will be apparent to those skilled in the relevant art that changes and modifications may be made to the invention described above without departing from its scope or spirit.

We claim:

1. A method of determining an accommodative range of an eye, comprising the steps of:

a) taking a first wavefront measurement of an eye using a wavefront sensor;

b) calculating a first effective clinical prescription using the first wavefront measurement;

c) adjusting the focusing optics of the wavefront sensor in a discrete step in the hyperopic direction;

d) taking a second wavefront measurement of the eye after adjusting the focusing optics of the wavefront sensor in the first discrete step in the hyperopic direction;

e) calculating a second effective clinical prescription using the second wavefront measurement;

f) determining the difference between the first effective clinical prescription and the second effective clinical prescription;

g) comparing the difference between the first effective clinical prescription and the second effective clinical prescription against an allowed tolerance;

h) repeating steps c) through g) until the difference between the first effective clinical prescription and the second effective clinical prescription is less than the allowed tolerance;

i) adjusting the focusing optics of the wavefront sensor in a discrete step in the myopic direction;

k) taking a third wavefront measurement of the eye after adjusting the focusing optics of the wavefront sensor in the first discrete step in the myopic direction;

l) calculating a third effective clinical prescription using the third wavefront measurement;

m) determining the difference between the second effective clinical prescription and the third effective clinical prescription;

n) comparing the difference between the second effective clinical prescription and the third effective clinical prescription against an allowed tolerance;

o) repeating steps i) through n) until the difference between the second effective clinical prescription and the third effective clinical prescription is less than the allowed tolerance; and p) calculating an accommodative range of the eye by comparing the effective clinical prescription taken at step l with the effective clinical prescription taken at step e.

2. A method of determining an aberration profile of an eye, comprising the steps of:

a) taking a first wavefront measurement of an eye using a wavefront sensor;

b) calculating a first effective clinical prescription using the first wavefront measurement;

c) adjusting the focusing optics of the wavefront sensor in a discrete step in the hyperopic direction;

d) taking a second wavefront measurement of the eye after adjusting the focusing optics of the wavefront sensor in the first discrete step in the hyperopic direction;

e) calculating a second effective clinical prescription using the second wavefront measurement;

f) determining the difference between the first effective clinical prescription and the second effective clinical prescription;

g) comparing the difference between the first effective clinical prescription and the second effective clinical prescription against an allowed tolerance;

h) repeating steps c) through g) until the difference between the first effective clinical prescription and the second effective clinical prescription is less than the allowed tolerance;

i) adjusting the focusing optics of the wavefront sensor in a discrete step in the myopic direction;

k) taking a third wavefront measurement of the eye after adjusting the focusing optics of the wavefront sensor in the first discrete step in the myopic direction;

l) calculating a third effective clinical prescription using the third wavefront measurement;

m) determining the difference between the second effective clinical prescription and the third effective clinical prescription;

n) comparing the difference between the second effective clinical prescription and the third effective clinical prescription against an allowed tolerance;

o) repeating steps i) through n) until the difference between the second effective clinical prescription and the third effective clinical prescription is less than the allowed tolerance; and p) calculating an aberration profile of the eye by comparing the effective clinical prescription taken at each iterative step.

* * * * *